(12) United States Patent
Burgio

(10) Patent No.: US 6,322,360 B1
(45) Date of Patent: *Nov. 27, 2001

(54) MEDICATION RETENTION ASSEMBLY FOR ORAL DELIVERY TRAY

(75) Inventor: Paul A. Burgio, Grant, MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/426,123

(22) Filed: Oct. 22, 1999

(51) Int. Cl.[7] .............................. A61G 17/02; A61C 3/00; A61C 5/00
(52) U.S. Cl. .................................. 433/80; 433/6; 433/215
(58) Field of Search ............................. 433/8, 9, 80, 215, 433/229, 6

(56) References Cited

U.S. PATENT DOCUMENTS

| Re. 34,196 | 3/1993 | Munro . |
|---|---|---|
| 1,934,688 | 11/1933 | Ackerman . |
| 2,257,709 | 9/1941 | Anderson . |
| 2,963,786 | 12/1960 | Browning . |
| 3,073,300 | 1/1963 | Berghash . |
| 3,247,844 | 4/1966 | Berghash . |
| 3,312,218 | 4/1967 | Jacobs . |

(List continued on next page.)

FOREIGN PATENT DOCUMENTS

| 1104116 | 6/1961 | (DE) . | |
|---|---|---|---|
| 29607299 | 10/1996 | (DE) . | |
| 2 002 637 | 2/1979 | (GB) . | |
| WO 98/30381 | 7/1998 | (WO) . | |
| WO 98/57564 | 12/1998 | (WO) . | |
| WO 94/23610 | 10/1994 | (WO) | ............................ A44B/18/00 |
| WO 97/11676 | 4/1997 | (WO) | ............................ A61K/7/20 |

OTHER PUBLICATIONS

BISCO, Insta–Brite, *Tooth Whitening System*, 2 pages.
Clinical Research Associates Newsletter, *Tooth Bleaching, State of Art 97*, vol. 21, Issue 4, Apr. 1997, p. 1–3.
*Computer Aided Design and Manufacture in Dentistry: A Review of the State of the Art*, from the Journal of Prosthetic Dentistry, vol. 58, p. 512 (1987).
*Three–Dimensional Dental Cast Analyzing System With Laser Scanning*, Kuroda, et al., Am. J. Ortho. Dent. Othrop., vol. 110[4], Oct. 1996, Pgs. 365–369.
"One Visit Insta–Brite Custom Bleaching System" brochure: Bisco, Inc.; 1997.
Home–Bleaching Technique Guide by Cary Goldstein, DDS; Dental Equipment and Supplies, Sep./Oct., 1998.
Pearl #2 by Joseph Blaos; Dental Economics; May, 1998.
Doctor's Instructions; Nupro Gold Tooth Whitening System; Dentsply International; Rev. Jul. 1997.

(List continued on next page.)

*Primary Examiner*—Nicholas D. Lucchesi
(74) *Attorney, Agent, or Firm*—James D. Christoff

(57) ABSTRACT

An assembly for retaining medication in an oral medication delivery tray includes a substrate, a layer of adhesive extending across the substrate and a release liner initially connected to the layer of adhesive. The assembly also includes a tab portion connected to the layer of adhesive and extending past the substrate. The tab portion serves as a handle to facilitate separation of the layer of adhesive from the release liner as the substrate is pulled away from the release liner, so that the layer of adhesive remains on the substrate.

23 Claims, 1 Drawing Sheet

U.S. PATENT DOCUMENTS

| | | |
|---|---|---|
| 3,379,193 | 4/1968 | Monaghan . |
| 3,404,056 | 10/1968 | Baldwin . |
| 3,496,936 | 2/1970 | Gores . |
| 3,527,219 | 9/1970 | Greenberg . |
| 3,624,909 | 12/1971 | Greenberg . |
| 3,688,406 | 9/1972 | Porter et al. . |
| 4,044,762 | 8/1977 | Jacobs . |
| 4,063,552 | 12/1977 | Going et al. . |
| 4,064,628 | 12/1977 | Weitzman . |
| 4,138,814 | 2/1979 | Weitzman . |
| 4,290,174 | 9/1981 | Kalleberg . |
| 4,368,040 | 1/1983 | Weissman . |
| 4,401,616 | 8/1983 | Wagner . |
| 4,560,351 | 12/1985 | Osborne . |
| 4,569,342 | 2/1986 | von Nostitz . |
| 4,776,792 | 10/1988 | Wagner et al. . |
| 4,984,339 | 1/1991 | Provost et al. . |
| 5,076,791 | 12/1991 | Madray, Jr. . |
| 5,078,599 | 1/1992 | Eenboom et al. . |
| 5,085,585 | 2/1992 | Zimble . |
| 5,098,303 | 3/1992 | Fischer . |
| 5,165,424 | 11/1992 | Silverman . |
| 5,221,202 * | 6/1993 | James ................................... 433/9 |
| 5,234,342 | 8/1993 | Fischer . |
| 5,240,415 | 8/1993 | Haynie . |
| 5,328,363 * | 7/1994 | Chester et al. ....................... 433/9 |
| 5,348,154 | 9/1994 | Jacobs et al. . |
| 5,354,199 * | 10/1994 | Jacobs et al. ......................... 433/9 |
| 5,376,006 | 12/1994 | Fischer . |
| 5,409,631 | 4/1995 | Fischer . |
| 5,460,527 | 10/1995 | Kittelsen . |
| 5,536,168 | 7/1996 | Bourke . |
| 5,562,449 | 10/1996 | Jacobs et al. . |
| 5,573,399 | 11/1996 | McClintock, II . |
| 5,575,654 | 11/1996 | Fontenot . |
| 5,575,655 | 11/1996 | Darnell . |
| 5,626,866 | 5/1997 | Ebert et al. . |
| 5,702,251 | 12/1997 | McClintock, II . |
| 5,707,235 | 1/1998 | Knutson . |
| 5,725,843 | 3/1998 | Fischer . |
| 5,746,598 | 5/1998 | Fischer . |
| 5,759,037 | 6/1998 | Fischer . |
| 5,759,038 | 6/1998 | Fischer . |
| 5,770,105 | 6/1998 | Fischer . |
| 5,816,802 | 10/1998 | Montgomery . |
| 5,842,860 | 12/1998 | Funt . |
| 5,863,202 | 1/1999 | Fontenot et al. . |
| 5,891,453 | 4/1999 | Sagel et al. . |

OTHER PUBLICATIONS

Patient Instructions; Nupro Gold Tooth Whitening System; Dentsply International; Rev. Sep. 1997.

Nite White Dentist and Laboratory Instructions; Discus Dental, Inc.; undated.

Day White Dentist and Laboratory Instructions; Discus Dental, Inc.; undated.

Recommended Procedures for Fabricating a Rembrandt Bleaching Mouthguard; Denmat Corporation; 1998.

Rembrandt Lighten Bleaching Gel Instructions for Dentists; Denmat Corporation; 1996.

Opalescence Tooth Whitening Gel; Ultradent Products, Inc.; 1997.

Opalescence Dentists Instructions; Ultradent Products, Inc.; 1997.

* cited by examiner

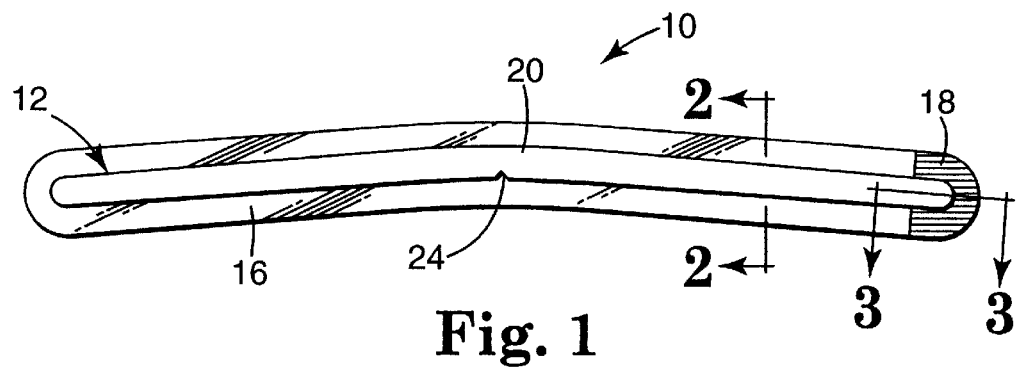
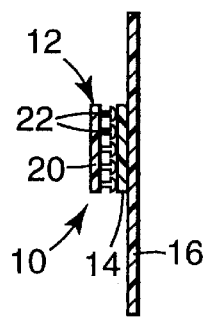
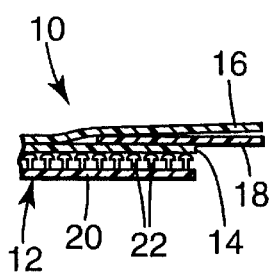
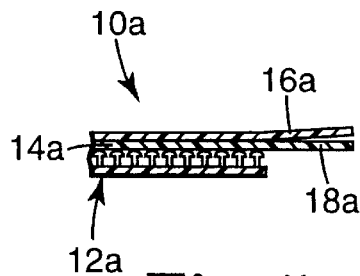
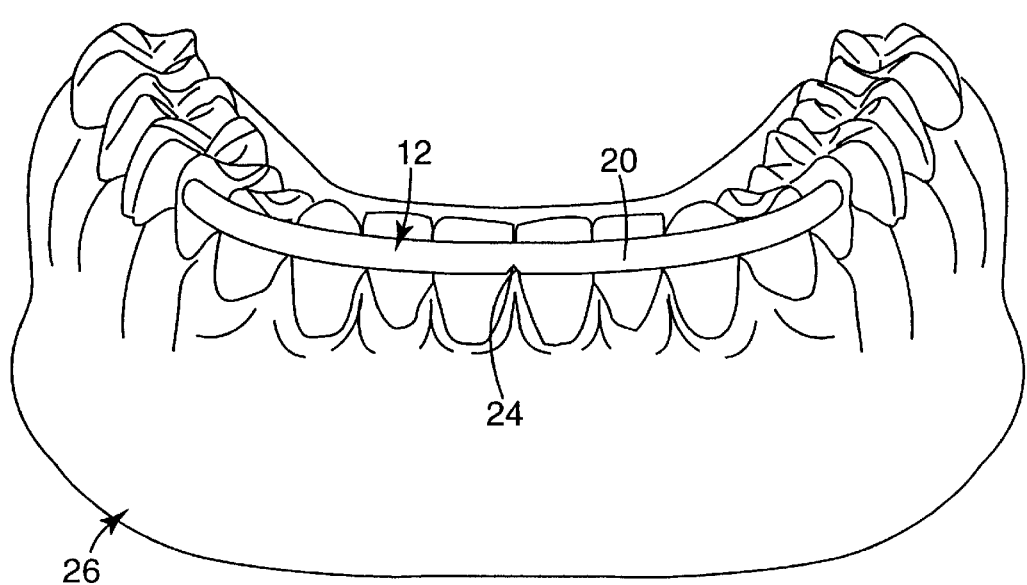

MEDICATION RETENTION ASSEMBLY FOR ORAL DELIVERY TRAY

FIELD OF THE INVENTION

The present invention broadly relates to structure and methods for delivering medication to the teeth and/or gingiva of a dental patient. More particularly, the field of the present invention concerns a medication retention assembly for a custom-made oral delivery tray that can be fabricated in a dental laboratory or in the practitioner's office.

DESCRIPTION OF THE RELATED ART

A variety of methods have been proposed in the past to deliver medication to the teeth and/or gingiva (i.e., the gum tissue) of a dental patient. One method of applying medication to teeth involves direct application of the medication to the tooth surface by the use of a brush, swab or the like. This method is relatively inexpensive and can be carried out either by the dental practitioner or by the patient.

Unfortunately, the direct application of a medicant to oral structures is generally unsatisfactory because the medication typically does not remain on the oral structure for a significant length of time. The length of time is variable and may depend on factors such as the viscosity of the medication, the presence of saliva and the ability of the patient to prevent adjacent soft tissues such as inner surfaces of the labia or lips and bucca or cheeks from contacting the tray containing the medication. In many instances, the effectiveness of the medication is substantially diminished if the medication is prematurely removed from the oral structure under treatment.

Another common method for delivering medication to teeth involves the use of a dental tray that is placed over the dental arch. The tray has a channel that receives the teeth and has a length that is sufficient to receive all or at least a portion of the dental arch. In some instances, the channel has a sufficient depth to receive a portion of the gingiva along with the teeth.

Many dental medication delivery trays are mass-produced and not custom made to closely fit the dental arch of a particular patient. Although such trays are relatively inexpensive, they are often considered quite bulky and unpleasant to wear for any significant length of time. Additionally, some mass-produced dental trays do not retain medication against the oral structures under treatment unless the patient remains relatively immobile.

Dental trays that are custom-made to closely fit the dental arch of a patient are considered by many to represent a significant improvement over mass-produced dental trays. The close fit provided by custom-made trays largely avoids unnecessary void spaces that are common with mass-produced dental trays. Most custom-made trays are less obtrusive in the mouth than mass-produced trays, and as such are more comfortable to wear for extended periods of time.

One technique of making a custom dental tray involves taking an alginate impression of a patient's dental structure, and then making a model or casting from the impression. Next, a thin sheet of heat softenable plastic material (such as a thermoplastic material) is placed over the casting and heated, often under vacuum, causing the plastic sheet to drape over the model and ultimately form a configuration that closely matches the shape of the underlying model. The tray is then trimmed as needed.

One of the most common uses of both mass-produced and custom-made dental medication trays is in connection with a bleaching gel or solution to whiten the patient's teeth. Many individuals desire whiter teeth and seek to eliminate or at least reduce the discoloration of stained teeth. Tooth stains are caused by a variety of sources, including food and beverages, drugs (such as tetracycline), tobacco products and poor oral hygiene.

When dental trays are used for bleaching teeth at home, the patient is typically instructed to place an amount of bleaching solution into a corresponding area of the tray for each tooth to be treated. The tray is then placed over the dental arch. Often, the bleaching solution is changed every 0.5 to 2.5 hours and the tray is removed during meals. Sometimes a recommendation is made to wear the dental tray overnight. The efficacy of the bleaching procedure depends on factors such as the type and intensity of the stain, the bleaching agent contact time on the tooth surfaces, the amount of available active ingredient in the bleaching solution as well as patient acceptance and adherence to the procedure.

Unfortunately, the volume of bleaching solution that is available in conventional trays tends to diminish rapidly over time, thereby decreasing the amount of active ingredient available for bleaching the teeth. Test results in the April, 1997 issue of the *Clinical Research Associates Newsletter* show that in many instances after 30 minutes, less than 50% of the original quantity of bleaching agent was available for bleaching activity. The same test results show that in many instances after one hour, less than 25% of the bleaching agent was available for bleaching activity. Consequently, it is often recommended to replenish the bleaching agents in conventional trays about every 15 to 30 minutes in order to maintain the most efficacious dosage of bleaching agent in contact with the tooth.

However, the daytime schedules of many patients do not easily accommodate periodic, continuous replenishment of the bleaching agent. In addition, periodically replenishing the bleaching agent during the night is unrealistic for many patients. Since patient adherence to the procedure determines the ultimate success of the treatment program, the need to constantly replenish the dental bleaching solution is a major obstruction that limits the success of the treatment.

An improved custom-made dental tray for delivering medication to oral structure is described in U.S. Pat. No. 6,126,443. The dental tray described in that reference has one or more medication reservoirs that each include a plurality of discreet support members projecting away from the reservoir to engage the dental structure of the patient. The support members are arranged to resist the flow of medication such as bleaching solution in a gingival direction so that retention of the solution in the tray is enhanced.

In certain embodiments of the custom-made dental tray described in U.S. Pat. No. 6,126,443, the reservoirs are made by placing one or more substrates over a mold, casting or other model of the patient's dental structure, and then forming a sheet member over the substrate(s) and the model to provide a custom-molded structure. The substrate(s) in preferred embodiments include a backing layer with a number of spaced apart protrusions extending from the backing layer in a direction toward the model. Once the tray is completed, removed from the model and placed in the oral cavity of the patient, the protrusions extend toward the patient's dental structure that is intended to receive the medication. The protrusions serve as the discreet support members mentioned above to facilitate retention of the medication (such as dental bleaching solution) in the tray.

In certain embodiments of the medication delivery tray described in U.S. Pat. No. 6,126,443, the substrate is elongated and of a size sufficient to extend over several model teeth. As a result, application of reservoir-making material to the surface of each model tooth on an individual basis can be avoided and the total time required to make the tray is substantially reduced. The tray is preferably made with the elongated substrate permanently bonded to the thermoplastic tray material, although as an alternative the substrate may be placed over the model teeth with its protrusions facing outwardly such that an impression of the substrate is formed in the thermoplastic material to create the discreet support members mentioned above.

The elongated substrate that is described in U.S. Pat. No. 6,126,443, is optionally supplied to the practitioner in an assembly (known as a dental medication retention assembly) that also includes a section of double-sided adhesive tape (i.e., a section of tape with adhesive on both sides) and a release liner. To use the substrate to make a dental delivery tray, the release liner is separated from the section of adhesive tape and discarded. Next, the remaining assembly of the substrate and the adhesive tape is placed over the stone model such that the side of the tape previously in contact with the release liner is placed on the surface of the stone model. Once the sheet of thermoplastic material is formed over the model and the substrate, the resulting dental tray is removed from the model. Preferably, the section of adhesive tape preferentially adheres to the model, so that as the tape is pulled from the model the adhesive detaches from the substrate and remains on the model. Medication such as a dental bleaching solution is then applied to the substrate in the tray and the tray is placed over the patient's dental arch.

In commercial embodiments of the medication delivery tray described in U.S. Pat. No. 6,126,443, the section of adhesive tape has essentially the same overall configuration as the adjacent substrate, while the release liner is significantly larger. To separate the release liner from the adhesive tape, the practitioner typically grasps the release liner with one hand and bends the release liner in a small arc away from the substrate in order to initiate separation of the adjacent end section of the adhesive tape and substrate. In most instances, the end sections of the substrate and adhesive tape simultaneously peel away as a single unit from the release liner as the release liner is bent back, so that the end sections can then be grasped and pulled away from the release liner with the other hand until such time as the release liner has disengaged the adhesive tape along its entire length.

Unfortunately, in some instances the adhesive tape does not separate from the release liner as intended and instead remains attached to the release liner while the substrate peels away from the adhesive tape. In that instance, the practitioner may completely detach the substrate from the adhesive tape before realizing that the tape has remained on the release liner. Such a situation represents a nuisance, because the tape must then be replaced on the substrate before the substrate can adhere to the stone model as intended.

In other situations, the practitioner may attempt to facilitate separation of the substrate and adhesive tape from the release liner by moving his or her fingernail toward the end section of the substrate and tape. However, in some instances, the fingernail may be unintentionally moved into a position between the substrate and the tape, instead of into a position between the tape and the release liner. When the substrate is subsequently pulled away from the release liner in that instance, the tape is likely to remain attached to the release liner and separate from the substrate.

The various inventions set out in U.S. Pat. No. 6,126,443, represent a significant advance in the art. However, as can be appreciated, there remains a need to avoid the problem of unintentional separation of the adhesive from the substrate as described above.

SUMMARY OF THE INVENTION

The present invention overcomes the problems noted above by provision of a tab portion that is connected to a layer of adhesive (such as a section of double-sided adhesive tape) of a dental medication retention assembly. The tab portion serves as a handle that can be readily grasped and pulled in a direction away from the release liner. Since the tab portion is connected to the layer of adhesive, the adhesive simultaneously detaches from the release liner as the tab portion is pulled away from the release liner, so that the layer of adhesive remains connected to the substrate in each instance.

More specifically, the invention in one aspect is directed to a medication retention assembly for an oral medication delivery tray. The assembly includes a substrate and a layer of adhesive extending across the substrate. The assembly also includes a release liner extending across the layer of adhesive and releasably connected to the layer of adhesive. The assembly also includes a tab portion connected to the layer of adhesive and extending past the substrate for facilitating separation of the layer of adhesive from the release liner.

In another aspect, the present invention is directed toward a method of making a medication delivery tray for delivering medication to dental structures of a patient. The method includes the act of providing a medication retention assembly having a substrate, an adhesive layer extending across the substrate and a release liner releasably connected to the adhesive layer. The method also includes the acts of grasping a tab portion connected to the adhesive layer, and urging the tab portion in a direction away from the release liner in order to separate the adhesive layer from the release liner. The method further includes the act of applying the substrate and the adhesive layer to a model of the patient's dental structure.

These and other aspects of the invention are described in detail in the paragraphs that follow and are illustrated in the accompanying drawings.

BRIEF DESCRIPTION OF THE DRAWINGS

FIG. 1 is a side elevational view of a medication retention assembly constructed in accordance with one embodiment of the present invention;

FIG. 2 is an end cross-sectional view (not to scale) taken along lines 2—2 of FIG. 1;

FIG. 3 is a fragmentary cross-sectional view (not to scale) taken along lines 3—3 of FIG. 1 and looking in a gingival direction;

FIG. 4 is a perspective view of an exemplary model of a patient's dental structure along with a portion of the medication retention assembly illustrated in FIGS. 1–3; and FIG. 5 is a view somewhat similar to FIG. 3 but showing a medication retention assembly according to another embodiment of the invention.

DETAILED DESCRIPTION OF THE PREFERRED EMBODIMENTS

A medication retention assembly for an oral medication delivery tray according to one embodiment of the invention is illustrated in FIGS. 1–3 and is designated by the numeral 10. The assembly 10 broadly includes a substrate 12, a layer of adhesive 14 (FIGS. 2 and 3), a release liner 16 and a tab portion 18.

Preferably, the substrate 12 includes a backing layer 20 and a plurality of protrusions 22 that are integrally connected to the backing layer 20. The protrusions 22 are shown in FIGS. 2–3 and can have a variety of geometric shapes in cross section, such as rectangular, circular, semi-circular, triangular, square, hexagonal and the like. The protrusions may also have a variety of overall shapes such as cones, truncated cones, rods, pyramids, truncated pyramids, cubes, gumdrops, cylinders, nail heads, mushroom-shaped members and the like.

Further, the outer ends of the protrusions 22 may be flat, rounded, pointed or a variety of other shapes. Optionally, the protrusions 22 and the backing layer 20 may be made by a micro-replication method such as the methods disclosed in U.S. Pat. No. 5,152,917 (Pieper et al.) and U.S. Pat. No. 5,500,273 (Holmes et al.).

Preferably, the protrusions 22 and the backing layer 20 present a medication receiving reservoir having a number of tortuous paths. A tortuous path refers to a passageway or conduit that is not substantially straight and extends past the sides of the protrusions 22 in the spaces between adjacent protrusions 22. The tortuous paths are preferably arranged to increase flow resistance in a gingival direction through the resulting reservoir (i.e., in a direction toward the patient's gums) and/or in a mesial-distal direction along the length of the tray channel (i.e., in a direction along the length of the dental arch). To the extent that any segment of the tortuous paths is straight, that segment is preferably skewed with respect to the gingival direction or the mesial-distal direction of the channel. Optionally, the protrusions 22 are constructed of a hydrophilic material.

In general, the number of protrusions 22 per unit area is preferably in the range of about 78 per square cm. (500 per sq. in.) to about 465 per sq. cm. (3000 per sq. in.). An example of a suitable number is about 144 per sq. cm. (900 per sq. in.). However, a higher or lower number of protrusions 22 per unit area may be optimal in certain circumstances and the optimal number may depend on factors such as the nature of the sheet member material (as described below) forming the tray, the characteristics of the medication and the height, shape and diameter of the protrusions 22. The height of the protrusions 22 is preferably in the range of about 0.5 mm. to about 1.5 mm., although longer or shorter protrusions 22 may be used for specific applications, depending upon the viscosity of the medication, the nature of the treatment, the specific dental structure being treated, etc.

The exemplary protrusions 22 that are illustrated in FIGS. 2 and 3 each include a stem that projects outwardly from the backing layer 20 as well as an enlarged head. Various manufacturing processes for forming an array of upstanding headed stems integral with a backing layer are described in U.S. Pat. No. 4,290,174 (Kalleberg) U.S. Pat. No. 4,984,339 (Provost et al.), WO 94/23610 (Miller et al.), WO 98/30381 (Miller et al.) and PCT/US97/15960 (Kempfer). An example of a suitable substrate is a die-cut section of the hook side of a polypropylene micro-replicated mechanical fastener such as no. CS-200 diaper tape from 3M Company.

The layer of adhesive 14 is preferably a section of adhesive tape that includes a membrane having opposite faces and a coating of adhesive extending across at least one face. More preferably, the layer of adhesive 14 is a medical grade double-sided pressure-sensitive adhesive tape such as #1522 from 3M Company. Optionally, the layer of adhesive 14 provides good adhesion in the presence of water. As an example, the layer of adhesive 14 could include a coating of adhesive (preferably medical-grade adhesive) that provides good adhesion in the presence of water; that coating may be placed on the release liner 16 and covered with a barrier layer (such as a coating of water based urethane) that, when dried, is placed into contact with one face of the double-sided adhesive tape mentioned above.

Preferably, but not necessarily, the layer of adhesive 14 has an overall configuration that is essentially identical to the overall configuration of the substrate 12 when considered in side elevational view (i.e., when looking toward the plane of the drawing of FIG. 1). Preferably, the substrate 12 and the layer of adhesive 14 have a length sufficient to extend across all of the tooth surfaces intended to receive medication. For example, the substrate 12 and the layer of adhesive 14 may have an overall length corresponding to the length extending mesially-distally along the dental arch from one of the second bicuspid teeth to the other. Alternatively, if the medication is intended to be applied to the molar teeth as well, the substrate 12 and the layer of adhesive 14 may be somewhat longer in order to extend over the molar tooth surfaces. Optionally, the substrate 12 and the layer of adhesive 14 may be trimmed by the practitioner as desired.

Preferably, a gingival edge of the substrate 12 (and optionally the layer of adhesive 14) includes a notch 24 that is located in the center of the substrate 12 along its length. The notch 24 provides a visual alignment guide to facilitate placement of the substrate 12 and the layer of adhesive 14 on a model of the patient's tooth structure. An example of a tooth structure model is the model 26 illustrated in FIG. 4 of the teeth and adjacent gingival tissue of an entire dental arch. However, the tooth structure model may be representative of only part of the dental arch, or of only one tooth if desired. The inclusion of gingiva on the model is also optional.

The release liner 16 facilitates handling of the assembly 10 before such time as the substrate 12 and the layer of adhesive 14 are applied to the model 26, and also protects the tacky layer of adhesive 14 from contamination by dust or other debris before application to the model 26. Suitable materials for the release liner 16 include a section of poly(ethylene terephthalate) ("PET") sheeting that is coated with silicone to enhance release of the adhesive. The release liner 16 preferably, but not necessarily, extends across and past the layer of adhesive 14 in directions along the longitudinal axis of the substrate 12 as well as in directions perpendicular to the longitudinal axis of the substrate 12, and is releasably connected to the layer of adhesive 14.

The tab portion 18 is connected to the layer of adhesive 14 and extends past the substrate 12. Preferably, but not necessarily, the tab portion 18 extends past the substrate 12 in directions parallel with the longitudinal axis of the substrate 12 as well as in directions perpendicular to the longitudinal axis of the substrate 12. Optionally, and as shown in FIG. 1, the tab portion 18 has an overall configuration that essentially matches an overall configuration of an end section of the release liner 16 when considered in side elevational view (i.e., when looking in a direction toward the plane of the drawing in FIG. 1). As another option, the tab portion 18 has an overall configuration that is different than the overall configuration of the end section of the release liner 16 (i.e., either stops short of or extends past the periphery of the end section of the release liner 16 in longitudinal and/or lateral directions).

One example of a suitable tab portion 18 is a section of flexible plastic material such as polyester. Optionally, and as illustrated in FIGS. 2 and 3, the tab portion 18 is releasably connected to the layer of adhesive 14 and is made as a section of material that is initially discreet from the layer of adhesive 14. As a result, the tab portion 18 can be pulled away and readily separated from the layer of adhesive 14 once the layer of adhesive 14 has been detached from the release liner 16.

As another alternative, the tab portion may be integral with the layer of adhesive. For example, and as shown in the alternative assembly 10a of FIG. 5, a layer of adhesive 14a may be integrally joined in end-to-end relationship with a tab portion 18a. In this embodiment, the layer of adhesive 14a may comprise a section of double-sided tape as described above with a membrane and a coating of adhesive on opposite faces of the membrane. The layer of adhesive 14a is releasably connected to a substrate 12a that is identical to the substrate 12 described above. The tab portion 18a may be trimmed from the membrane once the layer of adhesive 14a has been detached from an adjacent release liner 16a. In this alternative, the tab portion 18a and the layer of adhesive 14a may be manufactured by die-cutting a section of double-sided adhesive tape, and then removing, covering or rendering ineffective the adhesive extending across the tab portion 18a. Other configurations and methods of manufacture are also possible. In other respects, the assembly 10a is similar to the assembly 10.

Preferably, the tab portion 18 of the assembly 10 does not adhere to the underlying region of the release liner 16 to any significant degree. As such, the practitioner can easily grasp the tab portion 18 with one hand while the other hand of the practitioner is grasping the release liner 16, even when the practitioner is wearing gloves. For example, the practitioner may wipe a finger or thumb along the peripheral edge of the tab portion 18 in order to facilitate moving the tab portion 18 away from underlying regions of the release liner 16 so that the tab portion 18 can then be tightly gripped before pulling the tab portion 18 and the layer of adhesive 14 away from the release liner 16. As another alternative, the practitioner may bend the end section of the release liner 16 underlying the tab portion 18 in an arc away from the tab portion 18, so that the tab portion 18 can then be readily gripped for subsequent peeling of the tab portion 18 and the layer of adhesive 14 away from the release liner 16. Preferably, the tab portion 18 has a color that is visibly different than the color of the release liner 16 so that the presence of the tab portion 18 is apparent at first glance. For example, the release liner 16 may present a translucent, clear or somewhat white appearance, while the tab portion 18 may have a bright color such as blue or red. Preferably, the color of the tab portion 18 is also visibly different than the color of the substrate 12 and the layer of adhesive 14 to serve as a reminder to the practitioner that the tab portion 18 should be fully removed from the layer of adhesive 14 before placement of the substrate 12 and the layer of adhesive 14 on the model 26. Preferably, the substrate 12 and the layer of adhesive 14 are also clear, translucent or white in appearance.

Preferably, the assembly 10 is part of a kit that also includes a material for making a dental medication delivery tray. An example of a suitable material for making the delivery tray includes a sheet of thermoplastic material such as polypropylene, ethylene or vinyl acetate, including ethylene vinyl acetate ("EVA"). Suitable EVA materials include, for example, 0.04 in. (1.0 mm) thick EVA vacuum forming material (catalog no. 089-5003, from Patterson Dental Supply, Inc.). EVA is commercially available and approved for oral use by the U.S. Food and Drug Administration.

Preferably, the section of sheet material for making the delivery tray is easily thermoformed or vacuum formed over the model 26 using conventional techniques. Preferably, the section of sheet material has a thickness no greater than about 0.08 in. (2.0 mm) and is translucent.

Once the substrate 12 and the layer of adhesive 14 have been detached from the release liner 16 and the tab portion 18 has been detached or trimmed from the layer of adhesive 14, the substrate 12 and the layer of adhesive 14 are placed on the model 26. Preferably, the practitioner places the notch 24 along the midline (i.e., in the mesial-distal center of the dental arch of the model 26), so that the substrate 12 is properly centered on the model 26. The notch 24 provides a visual alignment guide to facilitate placement of the substrate 12 on the model 26. Preferably, the substrate 12 is aligned to the mid-third of the teeth of the model 26 in an occlusal-gingival direction as shown in FIG. 4 (i.e., in a direction extending from the outer ends or tips of the model teeth to the model gingiva).

Preferably, but not necessarily, the substrate 12 and the adhesive layer 14 are initially longitudinally curved in a wide arc when attached to the release liner 16 as can be observed by reference to FIG. 1. The arc-shaped configuration of the substrate 12 and the adhesive layer 14 facilitates conforming the substrate 12 to the buccolabial tooth surfaces of the model 26 as the substrate 12 is attached to the model 26. Optionally, the practitioner may apply finger pressure to the substrate 12 in areas extending over interproximal regions of the model dental arch in order to better conform the substrate 12 to the curvature of the individual model teeth.

Next, a dental medication delivery tray is formed over the model 26 and the substrate 12. For example, a sheet member of thermoplastic material may be thermoformed or vacuum formed over the model 26 and the substrate 12. Suitable thermoplastic materials include, for example, the EVA materials described above. Preferably, the substrate 12 both chemically and mechanically bonds to the thermoplastic material in order to remain non-removably affixed in place in the tray.

The resultant dental tray is then removed from the model 26. Preferably, the layer of adhesive 14 preferentially adheres to the model 26, so that as the tray is pulled from the model 26 the adhesive layer 14 detaches from the substrate 12 and remains on the model 26. The tray is then trimmed as desired.

Preferably, the tray is trimmed so that a lingual wall of the tray includes an outer edge that extends along a line that is spaced at least in part and preferably spaced along substantially its entire length at least 4 mm in a gingival direction from the gingival margin of the lingual side of the patient's dental arch receiving the tray. More preferably, the outer edge of the lingual wall extends along a line that is spaced at least in part (and more preferably is spaced substantially along its entire length) a distance of 6 mm in a gingival direction from the gingival margin of the patient's dental arch along its lingual side. Optionally, the outer edge of the lingual wall is spaced no greater than 20 mm and preferably less than 12 mm in a gingival direction at any point from the gingival margin of the lingual side of the dental arch.

The preferred spacing of the outer edge of the lingual wall as mentioned in the previous paragraph is provided at least in regions adjacent the patient's anterior teeth (i.e., in regions adjacent the patient's central and lateral incisors). Optionally, that edge approaches the gingival margin as either end of the channel of the tray is approached. For example, the edge may be as close as 2 mm, or optionally directly adjacent the patient's gingival margin in regions next to the patient's molar teeth.

As another option, the tray when made to fit the upper dental arch includes a palatal section that extends across a majority of the patient's palate and is integrally connected to the lingual wall of the tray. In that instance, the outer edge is spaced a distance greater than 12 mm from the gingival margin at least in regions next to the anterior teeth.

Preferably, the resulting tray has a buccolabial wall (i.e., a wall facing the patient's lips or cheeks) with an outer edge that extends along the gingival margin of the patient's dental arch on a buccolabial side of the teeth. Preferably, that edge is located up to 2.0 mm, and more preferably only up to 1.0 mm, in an occlusal direction from the gingival margin and does not contact the gingival margin of the patient's dental arch when the tray is in use in the oral cavity. Preferably, the outer edge on the buccolabial side has a scalloped configuration that precisely matches the contoured shape of the adjacent gingival margin. Alternatively, however, the outer edge on the buccolabial wall could extend along the gingival margin in a generally straight path and pass along the location of each tooth where the gingival margin reaches an apex in a gingival direction (i.e., the location of each tooth, typically near the center of each tooth, where the exposed enamel extends the greatest distance in a gingival direction; in this alternative, the buccolabial wall of the tray completely covers each gingival papilla that extends in an occlusal direction toward an interproximal region between adjacent teeth). The location of the outer edge on the buccolabial wall as described above helps ensure that the resulting tray does not irritate the soft gingival tissue of the buccolabial side of the dental arch.

Further details for trimming the resultant tray according to preferred techniques are described in applicant's U.S. Pat. No. 6,142,780, the disclosure of which is expressly incorporated by reference herein.

The example of the model 26 that is illustrated in FIG. 4 may be made using any one of a number of suitable techniques. One method of making the model 26 involves first taking an impression of the patient's dental structure using an alginate impression material or other suitable impression material. The model 26 may be a replica of either the patient's upper or lower dental arch, or alternatively of a replica of only part of the patient's upper or lower dental arch.

Moreover, any of the techniques described above for making a dental tray may include as an option the use of a dental model that is made using digital data instead of a dental model that is cast from a dental impression. For example, a model arch similar to the model 26 may be prepared by generating digital information defining the shape of the patient's dental arch, and then using the digital information to create the model. Optionally, the digital information may be created by the methods set out in PCT application no. WO 97/03622. In brief, PCT application no. WO 97/03622 describes a method of generating digital information of a patient's dental arches by making an impression of the patient's arches, and then removing a layer from the impression (or alternatively removing a layer from a model made from the impression) to obtain a flat surface; a video camera or other device is then used to collect digital data of the flat surface and the method is repeated; finally, the data is combined to provide a data set representative of the configuration of the patient's dental arches. Stereolithographic apparatus can then be used to make the model arch.

Other means for generating digital information of the patient's dental arch may also be employed. For example, the digital information may be generated electromechanically (e.g., by stylus scanning), by laser scanning, by photogammetry, by sonic ranging, by digital video scanning or magnetically. Examples of devices for generating the information are described in an article by Rekow entitled *"Computer Aided Design and Manufacture in Dentistry: A Review of the State of the Art"*, from the Journal of Prosthetic Dentistry, Vol. 58, page 512 (1987). Other examples are described in U.S. Pat. Nos. 5,078,599, 5,131,844, 5,338,198, 4,611,288 and 5,372,502 as well as in an article entitled *"Three-dimensional dental cast analyzing system with laser scanning"* (Kuroda, et al., Am. J. Ortho. Dent. Othrop., Vol. 110 [4], October 1996, pages 365–69).

The resulting medication delivery tray is particularly suited for patients who desire to bleach their teeth. A common dental bleaching agent contains about 10% to about 16% carbamide peroxide, also called urea hydrogen peroxide, urea peroxide, hydrogen peroxide carbamide and perhydrol-urea. Carbamide peroxide has been used by dental clinicians since the 1960's as an oral antiseptic. Tooth whitening was a side effect of extended contact time. Over the counter ("OTC") compositions of 10% carbamide peroxide are available as "Gly-Oxide" by Marion Laboratories and "Proxigel" by Reed and Carnrick. A preferred dental bleaching agent comprises 64.86% propylene glycol, 21.00% glycerol, 1.5% carboxypolymethylene (e.g. Carbopol brand No. 980), 2.34% tris(hydroxymethyl) aminomethane, 0.30% mint flavor and 10.00% carbamide peroxide, with the viscosity increased by adjusting the pH to about 5.8.

The substrate 12, the layer of adhesive 14 and the release liner 16 may be constructed other than as described above. Various alternative constructions are set out in applicant's U.S. Pat. No. 6,126,443, the disclosure of which is also expressly incorporated by reference herein.

A number of other possible modifications and additions will become apparent to those skilled in the art after reviewing the description above. For example, the assembly 10 may have two tab portions that are similar to tab portion 18 and are located adjacent both ends of the substrate 12. Accordingly, the invention should not be deemed limited to the specific, currently preferred embodiments that are described in detail above, but instead only by a fair scope of the claims that follow along with their equivalents.

What is claimed is:

1. As assembly for shaping a wall of an oral medication delivery tray comprising:
   substrate having an overall size that is no greater than the overall size of a wall of an oral medication delivery tray;
   a layer of adhesive extending across the substrate and detachably connected to the substrate;
   a release liner extending across the layer of adhesive and releasably connected to the layer of adhesive; and
   a tab portion connected to the layer of adhesive and extending past the substrate for facilitating separation of the layer of adhesive from the release liner.

2. A medication retention assembly according to claim 1 wherein the tab portion is releasably connected to the layer of adhesive.

3. A medication retention assembly according to claim 1 wherein the tab portion is integrally connected to the layer of adhesive.

4. A medication retention assembly according to claim 1 wherein the substrate has an elongated configuration, and wherein the tab portion extends past the substrate in directions parallel with the longitudinal axis of the substrate.

5. A medication retention assembly according to claim 1 wherein the substrate has an elongated configuration, and wherein the tab portion extends past the substrate in directions perpendicular to the longitudinal axis of the substrate.

6. A medication retention assembly according to claim 1 wherein the tab portion and the release liner are different colors.

7. A medication retention assembly according to claim 1 wherein the layer of adhesive includes a membrane having opposite faces and a coating of adhesive extending across each face.

8. A medication retention assembly according to claim 1 wherein the substrate has an elongated configuration with an overall length sufficient to extend across a plurality of teeth.

9. A medication retention assembly according to claim 8 wherein the layer of adhesive is co-terminus with the substrate.

10. A medication retention assembly according to claim 1 wherein the substrate includes a reservoir for medication.

11. A medication retention assembly according to claim 10 wherein the substrate includes a backing layer and a plurality of protrusions extending outwardly from the backing layer.

12. A medication retention assembly of claim 1 wherein the assembly is part of a kit, and wherein the kit includes a section of sheet material for making an oral medication delivery tray.

13. A medication retention assembly according to claim 12 wherein the kit also includes a quantity of medication.

14. A medication retention assembly according to claim 13 wherein the medication comprises a dental bleaching agent.

15. A medication retention assembly according to claim 1 wherein the tab portion does not adhere to the release liner.

16. A method of making a medication delivery tray for delivering medication to dental structure of a patient comprising the acts of:

providing a medication retention assembly having a substrate, an adhesive layer extending across the substrate and a release liner releasably connected to the adhesive layer;

grasping a tab portion connected to the adhesive layer;

urging the tab portion in a direction away from the release liner in order to separate the adhesive layer from the release liner; and applying the substrate and the adhesive layer to a model of the patient's dental structure such that the adhesive layer is in contact with the model.

17. A method of making a medication delivery tray according to claim 16 and including the act of separating the tab portion from the adhesive layer after the tab portion has been urged in a direction away from the release liner.

18. A method of making a medication delivery tray according to claim 17 wherein the act of separating the tab portion from the adhesive layer includes the act of trimming the tab portion.

19. A method of making a medication delivery tray according to claim 17 wherein the act of separating the tab portion includes peeling the tab portion away from the adhesive layer.

20. A method of making a medication delivery tray according to claim 16 wherein the act of applying the substrate to a model of the patient's dental structure includes the act of applying the substrate to a plurality of teeth of the model.

21. A method of making a medication delivery tray according to claim 16 and including the act of forming a section of sheet material over the substrate and the model.

22. A method of making a medication delivery tray according to claim 16 and including the step of applying a quantity of medication to the substrate.

23. A method of making a medication delivery tray according to claim 22 wherein the act of applying a medication to the substrate includes the act of applying the medication to a reservoir of the substrate.

* * * * *

UNITED STATES PATENT AND TRADEMARK OFFICE
CERTIFICATE OF CORRECTION

PATENT NO. : 6,322,360 B1
DATED : November 27, 2001
INVENTOR(S) : Burgio, Paul A.

It is certified that error appears in the above-identified patent and that said Letters Patent is hereby corrected as shown below:

Title page,
Item [56], under FOREIGN PATENT DOCUMENTS, please add:

-- WO 97/03622   2/6/97   WO   A61C   13/00 --

Column 7,
Line 42, insert -- ¶ -- preceding "Preferably,".

Column 10,
Line 47, delete "As" and insert in place thereof -- An --.
Line 49, insert -- a -- preceding "substrate".

Signed and Sealed this

Thirteenth Day of August, 2002

Attest:

JAMES E. ROGAN
Attesting Officer        Director of the United States Patent and Trademark Office